United States Patent [19]

Kotz et al.

[11] Patent Number: 4,892,546

[45] Date of Patent: Jan. 9, 1990

[54] ADJUSTABLE PROSTHESIS FOR A JOINT BONE

[75] Inventors: Rainer T. Kotz, Vienna, Austria; Hans E. Harder, Probsteierhagen, Fed. Rep. of Germany

[73] Assignee: Howmedica GmbH, Schoenkirchem, Fed. Rep. of Germany

[21] Appl. No.: 189,570

[22] Filed: May 3, 1988

[30] Foreign Application Priority Data

May 15, 1987 [DE] Fed. Rep. of Germany ....... 8706999

[51] Int. Cl.$^4$ .............................................. A61F 1/00
[52] U.S. Cl. ........................................ 623/18; 623/20; 623/22; 623/23; 623/38; 623/16
[58] Field of Search ....................... 623/18, 20, 22, 23, 623/16, 38

[56] References Cited

U.S. PATENT DOCUMENTS

| | | | |
|---|---|---|---|
| 3,900,025 | 8/1975 | Barnes, Jr. ............................. | 128/92 |
| 4,384,373 | 5/1983 | Sivash .................................... | 623/18 |
| 4,502,160 | 3/1985 | Moore et al. .......................... | 623/18 |
| 4,586,932 | 5/1986 | Scales ..................................... | 623/16 |

*Primary Examiner*—Richard J. Apley
*Assistant Examiner*—N. Paul
*Attorney, Agent, or Firm*—Peter C. Richardson; Lawrence C. Akers; Mark Dryer

[57] ABSTRACT

An adjustable prosthesis for a bone joint comprising a joint component, an elongated rod having a distal end and a proximal end, a drive trunnion connected to said rod through an angular gear, an elongated inner sleeve, an outer sleeve and means for preventing rotation of said inner sleeve within said outer sleeve, said elongated rod including a threaded spindle and said inner sleeve including a threaded spindle nut which cooperates with said threaded spindle to provide longitudinal adjustment of the inner sleeve relative to the rod, said inner sleeve being telescopically slidable within said outer sleeve but being prevented by said means from rotating within said outer sleeve, said outer sleeve being secured to said joint component, said elongated rod being supported at its proximal end in said joint component for rotation relative to the joint component by said drive trunnion and angular gear, said drive trunnion being rotatably supported in said joint component, and said elongated rod having means for being releasably fixed against said rotation.

9 Claims, 2 Drawing Sheets

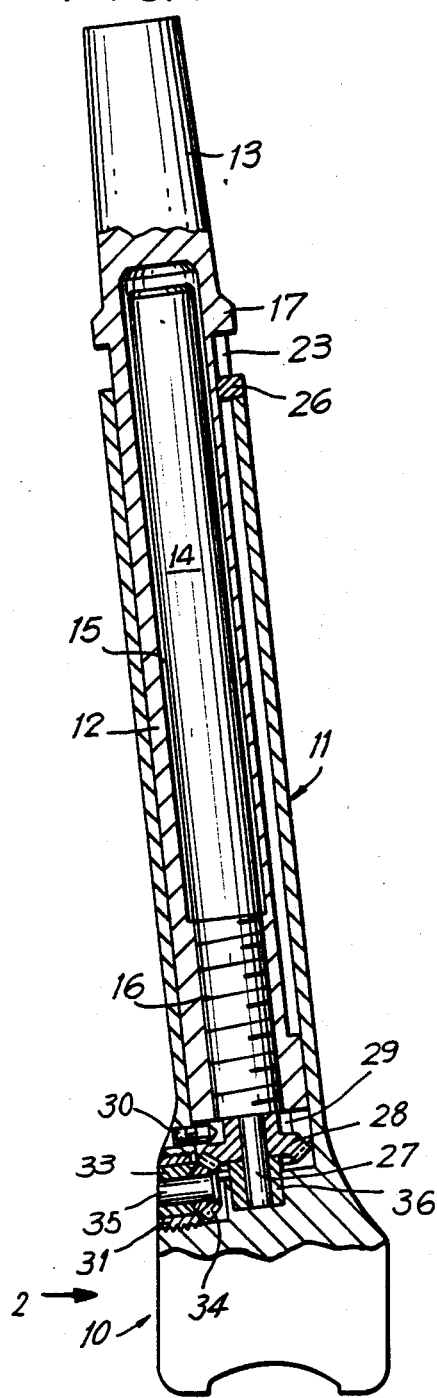
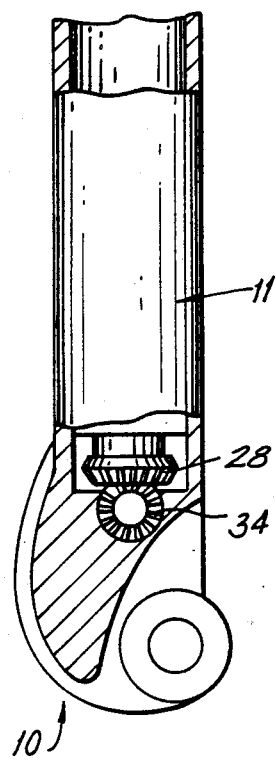
FIG. 1
FIG. 2

ADJUSTABLE PROSTHESIS FOR A JOINT BONE

BACKGROUND OF THE INVENTION

This invention relates to an endoprosthesis for femoral or tibial joint bone sections and adjacent femoral or tibial bone sections.

U.S. Pat. No. 4,578,081 discloses a bone prosthesis assembly for replacement of at least part of a natural joint of a patient wherein joint components can be connected to an elongation piece through a conical plug-in connection and the cones of the parts of the prosthesis define a self-locking connection. Since the prosthesis comprises a shank portion and a connection member adapted to be inserted in the bone by a set of elongation pieces of varying lengths, a relatively fine adaptation to varying lengths of the bone sections to be substituted can be made with a minimum stock expense. The self-locking cone connection provides a sufficient retaining force against the movement of the parts away from each other. Further, a considerable torque can be transferred thereby.

The above prosthesis can be varied in its length by using elongation pieces or joint components of different lengths. If an extension is necessary, a surgical operation must be carried out. Growing patients occasionally have to undergo multiple operations if the bone to be treated is to be adapted in its length to the length of the sound bone.

Therefore, it has been proposed to make a bone endoprosthesis continuously variable in its length to facilitate surgical operations. The endoprosthesis provided for this purpose consists of two telescopically co-operating rod portions. For example, one tubular rod portion is integrally formed with the joint portion and for example provided with an outer cone for the reception of a ball for a hip joint. The rod portion rotatably supports a nut co-operating with a threaded spindle of a second rod portion. A knee joint portion can be mounted, for example, on the outer end of the threaded spindle. The spindle nut is provided with an outer bevel-gear adapted to co-operate with the bevel-gear of a tool and is known in connection with drill chucks or the like.

The last-mentioned endoprosthesis has some deficiencies. A step is formed between both rod portions by which the patients may be affected: further, the soft tissue can be injured. The threaded spindle is directly located in soft tissue so that the latter may ingrow in the threads and disturb the adjustment of the threaded spindle. Conversely, adjustment of the threaded spindle may hurt the soft tissue. The adjustment drive for the threaded spindle is located between the ends of the endoprosthesis and thus is surrounded more or less by soft tissue. A post-operative adjustment of the length of the endoprosthesis thus requires a relatively extensive operation again.

In contrast to the above prior art, the present invention provides an endoprosthesis which is variable in length, can be simply adjusted post-operatively and does not injure soft tissue when adjusted and used.

SUMMARY OF THE INVENTION

In accordance with the present invention there is provided an adjustable prosthesis for a bone joint comprising a joint component, an elongated rod having a distal end and a proximal end, a drive trunnion connected to said rod through an angular gear, an elongated inner sleeve, an outer sleeve and means for preventing rotation of said inner sleeve within said outer sleeve, said elongated rod including a threaded spindle and said inner sleeve including a threaded spindle nut which cooperates with said threaded spindle to provide longitudinal adjustment of the inner sleeve relative to the rod, said inner sleeve being telescopically slidable within said outer sleeve but being prevented by said means from rotating within said outer sleeve, said outer sleeve being secured to said joint component, said elongated rod being supported at its proximal end in said joint component for rotation relative to the joint component by said drive trunnion and angular gear, said drive trunnion being rotatably supported in said joint component, and said elongated rod having means for being releasably fixed against said rotation.

In a particularly preferred embodiment of the invention rotation of said elongated rod relative to said joint component is achieved by a drive trunnion connected to said rod through an angular gear, said drive trunnion being rotatably supported in said joint component.

Also the particularly preferred means for preventing rotation of said inner sleeve within said outer sleeve comprises an inwardly facing projection in said outer sleeve which engages with a longitudinal slot in said inner sleeve.

DETAILED DESCRIPTION OF THE INVENTION

In the endoprosthesis according to the invention the spindle nut is formed by an elongated sleeve having an inner thread, the elongated sleeve being telescopically slidable within an outer sleeve connected to the joint component. The elongated rod including the threaded spindle within the spindle nut sleeve is capable of being fixed against axial movement and is supported for rotation within the joint component. The elongated rod is connected to a drive trunnion through an angular gear, the drive trunnion being rotatably supported in the joint component.

The outer sleeve and the inner spindle nut sleeve form two telescopically co-operating tubes. The irregularity of the outer diameter of the bone substituting portions thus is in the limitation of the difference between the outer diameter of the outer sleeve and the outer diameter of the spindle nut sleeve. This difference is relatively small and does not cause any soft tissue damage. During an adjustment of the endoprosthesis only a longitudinal displacement occurs which can be easily carried out without injuring the patient. It is significant to the preferred embodiment of the invention that the angular gear is located in the joint component of the endoprosthesis. Both in the knee joint area and in the hip joint area larger portions have a relatively small covering of soft tissue so that a simple access to the angular gear may be achieved by a simple puncture incision. It requires merely a local anaesthetic to change the length of the endoprosthesis. Therefore, the change in length may be made in a short time without burdening the patient too much.

With the prosthesis according to the invention, a large operation is not required for future adjustment, a relatively simple procedure may be followed. Further, more sharp edges leading to damage of the soft tissue are avoided. The adjustment mechanism according to the prosthesis of the invention is integrally mounted in the prosthesis thus protecting the soft tissue and avoiding injury of the soft tissue upon actuation.

The endoprosthesis according to the invention is adapted to substitute the total femur or tibia. Also, it may replace replace a joint section and the adjacent bone section. In this case, a bone splice portion can be connected to the bone substitution portion for the attachment to a sound bone portion. This connection between the endoprosthesis and a splice portion can be made through a self-locking cone connection. If the total bone is substituted, the endoprosthesis according to the invention may ave an inner or an outer cone for connection to a joint portion which has an outer or an inner cone.

In order to avoid a rotation of the spindle nut sleeve relative to the outer sleeve, an embodiment of the invention includes an inwardly facing projection on the outer sleeve, preferably located at the end thereof, which projection engages a longitudinal slot in the nut sleeve. According to a further embodiment of the invention, the slot includes at the lower end thereof, a circumferentially offset longitudinal lower slot portion which is connected to the remaining longitudinal slot through a circumferentially extending slot portion. By this, the spindle nut sleeve is axially secured in the outermost extended position.

As already mentioned, the elongated rod is rotatably supported within the joint component. In an embodiment of the invention the proximal end of said elongated rod includes a bearing extension supported within a bearing brushing in said joint component. The angular gear preferably comprises two bevel gears, one of which is connected to the bearing extension on the proximal end of said elongated rod while the other is connected to the drive trunnion. The bevel gear of the elongated rod, for example, can be engaged with the bevel gear on the drive trunnion with the front surface co-operating with the associated front surface of the bearing bushing. Also the drive trunnion can be supported by a bearing bushing which also provides a limitation for the drive trunnion outwards of the bearing bushing. The bearing bushing in turn can be threaded into a bore in the joint component.

An adjusted relative position of the elongated rod of the endoprosthesis according to the invention should not be changed if possible. Therefore, an embodiment of the invention provides a circumferentially extending groove between the bevel gear on the threaded spindle and a radial shoulder formed by the proximal end of said elongated rod, said groove being engaged by a set screw which is capable of being tightened or loosened. Thus, by means of the set screw the elongated rod can be secured against rotation, but released, when desired, to allow adjustment.

DESCRIPTION OF THE DRAWINGS

The invention will be described in more detail with reference to the preferred embodiments illustrated in the accompanying drawings, in which:-

FIG. 1 is a side elevation in partial cross section of an endoprosthesis according to the invention.

FIG. 2 is an end elevation of the lower portion of the prosthesis of FIG. 1 viewed in the direction of arrow 2.

Figure 3:
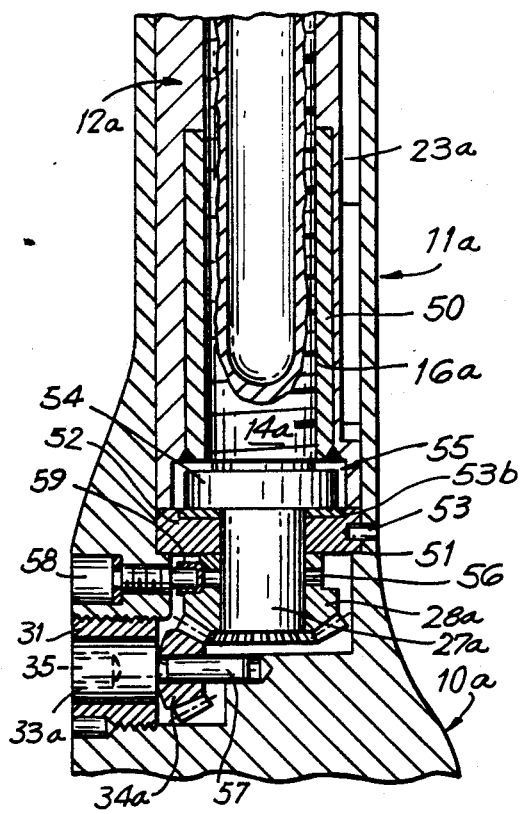
FIG. 3 is cross section through the tibial portion of an endoprosthesis according to FIG. 1 on an enlarged scale and somewhat modified.

The endoprosthesis illustrated in FIG. 1 and FIG. 2 includes a femoral knee joint component 10, the structure of which is not explained in detail. It co-operates with a tibial knee joint component not shown in the drawing. An outer sleeve 11 is connected to the joint component 10. An inner sleeve 12 including a threaded spindle nut is telescopically slidable within the outer sleeve and includes an outer cone 13 at the distal end thereof. A threaded spindle 14 is positioned within sleeve 12.

Figure 4:
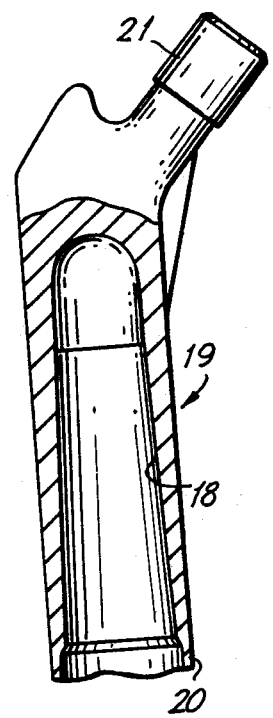
FIG. 4 is a cross-section of a joint portion adapted to be connected to the endoprosthesis of FIG.1.
Figure 5:
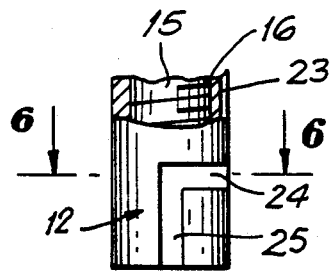
FIG. 5 is a side view of the lower part of the inner sleeve of FIG. 1.
Figure 6:
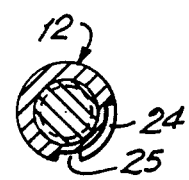
FIG. 6 is a cross section through line 6—6 of FIG. 5.

The structure of the spindle nut sleeve 12 is seen in FIG. 1. The inner bore 15 of sleeve 12 includes a threaded portion 16 only adjacent the open end thereof. The diameter of bore 15 is slightly larger than the inner diameter of the threaded portion 16. A flange 17 is integrally formed with sleeve 12 below a cone 13. The cone 13 serves to receive for example, an inner cone 18 of a femoral hip joint component 19 illustrated in FIG. 4. The cones 13, 18 co-operate self-lockingly.

A nose 20 of the joint component 19 co-operates with an appropriate recess in cone 13 and thus determines the relatively rotational position of both parts. The joint component 19 has a further cone 21 for receiving a joint ball. Instead of the joint component 19, a splice component or an extension component, respectively, can be used. In the first case, the cone 13 could be replaced by an inner cone which engages an outer cone of a splice component not shown.

The sleeve 12 has an axial parallel longitudinal slot 23 on the outer side thereof. The slot terminates in a slot portion 24 extending circumferentially, the slot portion 24 terminating in an axial parallel longitudinal slot portion 25 at the opposite end thereof. As can be seen in FIG. 1, the outer sleeve at the free end thereof includes a radially inwardly facing projection 26 engaging the longitudinal slot 23. Upon insertion of the inner sleeve 12 into the outer sleeve 11 first the projection 26 engages the lower slot portion 25. Thereafter the sleeve 12 is rotated a certain amount (quarter turn) until the projection can enter slot 23.

The elongated rod including threaded spindle 14 is provided with bearing extension 27 supporting a bevel gear 28 capable of being secured against rotation. The extension 27 protrudes beyond the bevel gear 28. Individual circumferentially spaced depressions 29 are provided in the bevel gear 28. In FIG. 1 a set screw 30 is inserted in the joint component 10, the set screw 30 extending into a groove which is formed between the bevel gear 28 and the lower end of the elongated rod. In the embodiment shown, this set screw 30 engages a depression 29 and thus prevents rotation of the elongated rod.

A bearing bushing 31 is threaded into a bore of the joint component 10. It serves for the support of a trunnion 33 having a bevel gear 34 at its inner end, the bevel gear 34 meshing with the bevel gear 28 of the elongated rod. The trunnion 33 includes a hexagonal recess 35 into which a rotating tool can engage.

The portion of the extension 27 extending beyond the bevel gear 28 engages a bearing bushing 36 which is located in the joint component 10. Thus, the bevel gear 28 slides on the associated end surface of the bearing bushing 36.

As can be seen in FIG. 1, a rotation of the trunnion 33 results in a rotation of the bevel gear 34 which in turn rotates the bevel gear 28 and thus also the elongated rod carrying threaded spindle 14. By this rotation, the inner sleeve 12 is moved longitudinally and slides outwards of the outer sleeve 11. The location of the drive trunnion and angular gear is such that easy access is achieved. As known, the area of the knee is covered by soft tissue only to a small extent.

The drive mechanism according to FIG. 3 deviates from that of FIG. 1 only with respect to some items. As far as the same parts are used, they are provided in FIG. 3 with the same reference numbers which bear the additional index a.

A sleeve 50 is slid into an enlarged portion of the threaded sleeve 12a and attached by welding. The sleeve is provided with a threaded portion 16a cooperating with the thread of the threaded spindle 14a. In FIG. 3 the threaded spindle is hollow to save weight and material.

The bore of shank 11a includes a shoulder 51 adjacent the joint portion 10a upon which a ring 52 is seated. Ring 52 is fixed by means of set screw 53 extending through the wall of shank 11a. A washer 53b is located in a recess in the upper surface of ring 52. The cylindrical extension 27a of the threaded spindle 14a extends through the bore of ring 52. An annular flange 54 is integrally formed on spindle 14a above the extension 27a. The annular flange is positioned within a free space 55 formed by an enlargement of the diameter of sleeve 12a below sleeve 50. The threaded spindle 14a is supported by ring 52 through the annular flange 54, the ring thus taking over the axial load on the joint component 10a.

The gear 28a is attached to the extension 27a by means of pins 56. It is free of axial loads. It meshes with gear 34a which is integrally formed with the drive trunnion 33a. The trunnion 33a is rotatably supported in the threaded sleeve 31a and includes a hexagonal recess 35a for a rotating tool. The back surface of the gear 34a having a larger diameter secures the gear 34a and the trunnion 33a, respectively, against axial outward movement. A bearing pin 57 is centrally received by the gear 34a opposite the trunnion 33a to improve the axial bearing of gear 34a.

A set pin or set screw 58 having a stepped outer diameter is received by a corresponding threaded bore of the joint portion 10a. The inner end retains an annular segment U-shaped in cross section for locking the gear 28a. The annular segment enables the distribution of the thrust load about a certain circumferential area of the gear 28a.

We claim:

1. An adjustable prosthesis for a bone joint, comprising a joint component, an elongated rod having a distal end and a proximal end, a drive trunnion connected to said rod through an angular gear, an elongated inner sleeve, an outer sleeve and means for preventing rotation of said inner sleeve within said outer sleeve, said elongated rod including a threaded spindle and said inner sleeve including a threaded spindle nut which cooperates with said threaded spindle to provide longitudinal adjustment of the inner sleeve relative to the rod, said inner sleeve being telescopically slidable within said outer sleeve but being prevented by said means from rotating within said outer sleeve, said outer sleeve being secured to said joint component, said elongated rod being supported at its proximal end in said joint component for rotation relative to the joint component by said drive trunnion and angular gear, said drive trunnion being rotatably supported in said joint component, and said elongated rod having means for being releasably fixed against said rotation.

2. A prosthesis according to claim 1, in which said means for preventing rotation of said inner sleeve within said outer sleeve comprises an inwardly facing projection in said outer sleeve which engages with a longitudinal slot in said inner sleeve.

3. A prosthesis according to claim 2, in which said slot includes, at the lower end thereof, a circumferentially offset longitudinal lower slot portion which is connected to the remaining longitudinal slot through a circumferentially extending slot portion.

4. A prosthesis according to claim 1, in which the proximal end of said elongated rod includes a bearing extension supported within a bearing bushing in said joint component.

5. A prosthesis according to claim 4, in which said bearing extension carries a fixedly attached bevel gear having an end surface which coacts with an end surface of said bearing bushing.

6. A prosthesis according to claim 1, in which said drive trunnion carries a bevel gear which engages with a bevel gear fixedly attached to a bearing extension on the proximal end of said elongated rod and said drive trunnion is supported by a bearing bushing.

7. A prosthesis according to claim 6, in which said bearing bushing which supports said drive trunnion is threaded into a bore in the joint component.

8. A prosthesis according to claim 5, in which a circumferentially extending groove is formed between said bevel gear and a radial shoulder formed by the proximal end of said elongated rod and said groove is engaged by a set screw which is capable of being tightened or loosened to, respectively, prevent or allow rotation of said elongated rod.

9. A prosthesis according to claim 1, in which said elongated rod includes an annular flange at its proximal end, which flange cooperates with a bearing ring in the joint component.

* * * * *